United States Patent [19]

Juge et al.

[11] Patent Number: 4,952,740
[45] Date of Patent: Aug. 28, 1990

[54] CYCLIC PHOSPHONITES

[75] Inventors: Sylvain Juge, Puteaux; Yvonne Legras, Paris, both of France

[73] Assignee: Societe Nationale Elf Aquitaine, France

[21] Appl. No.: 407,702

[22] Filed: Sep. 12, 1989

Related U.S. Application Data

[63] Continuation of Ser. No. 15,166, Feb. 17, 1987, abandoned, which is a continuation-in-part of Ser. No. 719,473, Apr. 3, 1985, abandoned.

[30] Foreign Application Priority Data

Apr. 10, 1984 [FR] France ............................... 84 05622

[51] Int. Cl.$^5$ .............................................. C07F 9/547
[52] U.S. Cl. ..................................................... 558/83
[58] Field of Search ......................................... 558/83

[56] References Cited

FOREIGN PATENT DOCUMENTS 3512781 10/1985 Fed. Rep. of Germany .
2158441 11/1985 United Kingdom .

*Primary Examiner*—Anton H. Sutto
*Attorney, Agent, or Firm*—Ostrolenk, Faber, Gerb & Soffen

[57] ABSTRACT

New cyclic phosphonites, in which one of the oxygen atoms of the ring can be replaced by an atom of sulphur or nitrogen; the molecule has an asymmetry due to at least two carbon atoms, one or more nitrogen and/or oxygen atoms or several of these elements together.

Preparation of these phosphonites by the reaction of a dihalogeno-phosphine with a compound having two active H atoms, in the presence of a hydracid acceptor.

Application of the new phosphonites to the production of the corresponding phosphinates and phosphine oxides.

14 Claims, No Drawings

CYCLIC PHOSPHONITES

This is a continuation of application Ser. No. 07/015,166 filed on Feb. 17, 1987, now abandoned, which is a continuation-in-part of application Ser. No. 719,473, filed Apr. 3, 1985, now abandoned.

The present invention relates to a new type of cyclic phosphonites and their oxides; it also comprises a process for the production of these compounds, as well as certain uses of the latter. More particularly, the invention makes possible the production of various optically-active compounds from quite simple and easily-obtainable starting materials, with good yields and a high optical purity.

The utility of organic phosphorus compounds and, in particular, optically-active compounds is well known at the present time. It is known that numerous natural and synthetic products can be prepared now by asymmetric synthesis, catalyzed by means of transition metals and particularly with catalysts comprising optically-active organophosphorus ligands. Substances of interest in agriculture, food production, pharmacy and perfumery can thus be prepared. The production of L-Dopa, so useful in therapeutics, in particular for the treatment of Parkinson's disease, is an example. The development and study of these syntheses are limited at present by difficulty in preparing optically-active organophosphorus ligands which are very often employed in asymmetric catalysts.

Useful organophosphorus compounds are in particular the phosphinates, from which phosphinamides, phosphines, phosphine oxides, phosphoniums, phosphinimides and other desired derivatives can be obtained. The economical preparation of phosphinates is thus of importance; the methods employed up to now have the disadvantages of requiring an expensive primary material and/or too large a number of operative steps. There is a process using menthyl phosphinate and another which begins with a 1,3,2-oxazaphosphole and requires the use of an organometallic reactant. Progress has been made by the Applicants by the use of 1,3,2-oxaza-phospholidines, with the intermediate formation of phosphinamides, but production of the phosphinate still comprises three stages counting from the diamino-phosphine which serves for preparation of the oxaza-phospholidine. Phosphinates have recently been obtained by the action of alkyl halides on the cyclic phenyl phosphonite of 1-methyl-trimethylene, by the locally selective opening of the ring of the phosphonite. However, the yield of this operation leaves much to be desired and the cyclic phosphonite itself is only obtained from the dichlorophenylphosphine in a yield of 62%. It is also considered that, when going on to other optically-active derivatives, the products should be purified by chromatography.

The present invention allows the above-mentioned process of locally selective opening to be realised in an improved manner, particularly with better yields and higher optical purities.

In the first place, the invention resides in the use of new cyclic phosphonites, one of the ring oxygen atoms of which can be replaced by a sulphur or nitrogen atom, the molecule of these compounds having an asymmetry due to at least two carbon atoms, to one or more nitrogen and/or oxygen atoms or to several of these elements together. Thus, the first material, which is subjected to locally selective opening of the ring, has a more marked asymmetry than the phosphonites described up till now.

The new products according to the invention can be represented by the general formula (1) below:

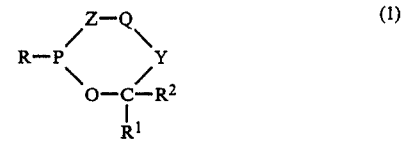

Z designates O, S or NH, the H of which can be replaced by a hydrocarbon radical which may be substituted; R, $R^1$ and $R^2$ are the same or different and each represents alkyl or alkenyl groups, preferably from $C_1$ to $C_{18}$, or cycloalkyl or aryl groups, preferably with one or two rings, and these radicals may carry substituents such as halogens, nitro, nitriles, amide, ester, ether, acetal or lactone; also $R^1$ and/or $R^2$ can be H atoms.

Y can constitute a simple bond between

and Q, in which case the ring contains 5 elements; but Y preferably forms an aliphatic chain or an aliphatic or aryl ring, providing 2 to 5 elements for the oxyphosphorus ring, so that the latter comprises 6 to 9 elements. When Y is thus a chain or a ring, for example:

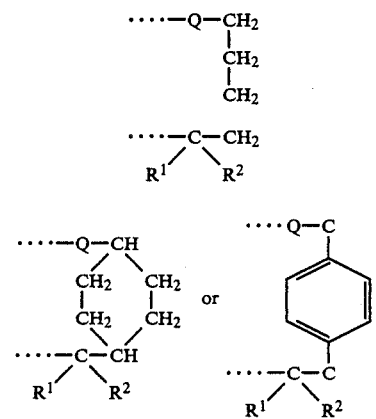

all or some of the H atoms of the compound can be replaced by aliphatic or aryl radicals and/or by functional groups, particularly such as those mentioned above in relation to R to $R^2$.

Q represents a group which can be of the same type as that of the lower part of formula (1), namely:

$R^3$ and $R^4$ having the same definition as $R^1$ and $R^2$ but they can be different from the latter.

Another form of Q is an aliphatic or aryl ring on which various substituents can be attached, in particular those which have been indicated above. Such a ring can equally form part of a metallocene.

According to a variant, Q itself constitutes a metallocene, for example ferrocenyl, chromocenyl or others. Also, it can form a group

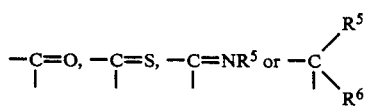

where $R^5$ and $R^6$ are defined like the radicals R, $R^1$, $R^2$ above.

It will be understood that, depending upon the nature of Z in the new compounds according to the invention, the nomenclature changes: When Z is a sulphur atom, the compound is in fact an oxathiaphospholane and if Z is an =NH or =NR, the product is an oxazaphospholidine of the type referred to in French Patent Application No. 8123153. However, for simplicity, reference will continue to be made in the present description to cyclic phosphonites in relation to all the compounds corresponding to the formula (1).

As already indicated above, an important characteristic of the new products according to the invention is the marked asymmetry of their molecules. Quantitatively, this property can be expressed by the ratio between the molecular weights of the two parts of the molecule situated on one side and the other of the X-X' plane passing through P and the region of Y, perpendicular to the plane of the formula (1) set out below:

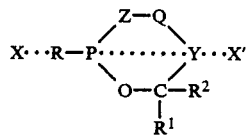

Thus, $M_1$ is the molar weight of and $M_2$ that of

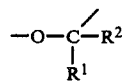

The preferred ratio $M_1:M_2$ (or $M_2:M_1$ if $M_2 < M_1$) is, according to the invention, equal to at least 3; it is preferably in the range from 3 to 10 and more preferably between 3 and 7. Greater asymmetries are not found in the prior art.

However, in the foregoing, mention has been made that Y is not only a simple bond or a single substituted C, through which the plane X-X' passes. In the more general case, where Y is a chain, it is necessary to take account as in the following example.

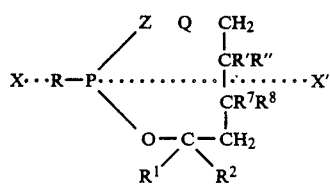

(2)

$M_1$ is the molecular weight of Z—Q—CH$_2$CR'R'', $M_2$ that of

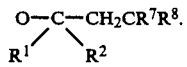

Preferably the greater ratio, $M_1:M_2$ or $M_2:M_1$, is at least 3 and particularly 3 to 10.

It will be noted that this ratio was much lower in the phosphonite of the prior art ("The Chemistry Society of Japan"—"CHEMISTRY LETTERS" pp. 913–916, 1983).

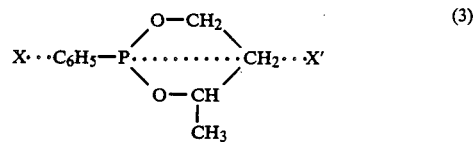

(3)

$M_1 = -O-CH_2- = 30 \quad M_2 = -O-CH-CH_3 = 44$
$M_2:M_1 = 44:30 = 1.47$

Experiments show in an unexpected manner that the Arbuzov reaction, that is opening the phosphonite ring under the action of an alkyl halide, occurs much better when the phosphonite has an asymmetry corresponding to higher $M_2:M_1$ ratios, according to the invention.

All the foregoing applies equally to the corresponding oxides of the phosphonites described, that is to compounds of the general formula:

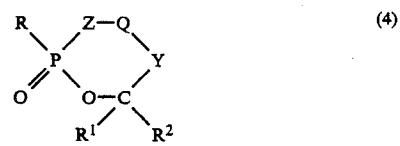

(4)

which form part of the invention.

The new products according to the invention can be prepared from a dihalogenophosphine by a process which is somewhat analogous to that of the known technique, but is characterized in that the compound having two groups, reacting with halogens of the phosphine, is selected from special compounds of the type

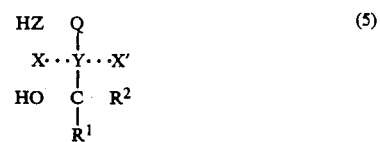

(5)

where the symbols Z, Q, Y, $R^1$ and $R^2$ have the same significance as above; the preferred ratio between the molecular weights of the two parts of the molecule situated on one side and the other the plane X-X' is at least 3 and is more particularly in the range from 3 to 10. The best values of this ratio are about 3 to 7.

As can be seen, the at least difunctional compound (5) can be a diol, alcohol-phenol, alcohol-thiol, alcohol-enol, alcohol acid or amino alcohol, in view of the various possible functions for ZH. The two functions, OH and ZH, can be located in different respective positions, but more particularly α, β, γ, δ or ε with respect to one another. Designated here generically by the term phosphonites, these compounds are particularly, the 1,3,2-dioxa-, oxathia- or oxaza-phospholanes, phosphorinanes or phosphonanes.

The reaction of dihalogeno-phosphine, for example a dichloro-alkyl or aryl phosphine, R-PCl₂, with a compound of the formula (5), produces 2 HCl per mole of phosphine; this acid is eliminated by a neutralizing agent or by an appropriate base, added to the reaction medium; this generally comprises a solvent for the reacting materials. Preferably, the neutralizing agent and the solvent are selected so that the halide which forms, particularly the chloride, precipitates. Neutralization can be effected with the aid of amines, particularly tertiary; notably pyridine, triethylamine, tributylamine etc. are particularly suitable, especially with tetrahydrofuran or toluene as the solvent, in which their hydrochlorides are insoluble. According to a feature of the invention, the base is employed in an excess of 3% to 12% with respect to the stoichiometric quantity necessary.

While the reaction can be carried out at temperatures from about −5° to +25° C., according to a preferred feature of the invention, operation takes place between −3° and +5° C. and particularly between −2° and +4° C.

The new cyclic phosphonites according to the invention are suitable for various direct applications, particularly as ligands for transition metals; this complexing property permits their use in the selective extraction of metals or in the formation of complex metallic catalysts. Phosphonites also serve as additives to plastics materials, in particular for stabilization and flame-retardancy. It is known also that pesticides, particularly fungicides, can be based on these compounds. When the part —Q—Y—, of the molecule (formula 1 or 4) is present in an antibiotic molecule, the phosphonite has improved biocidal properties; this is the case for example where the molecule (5) is derived from chloramphenicol. Complexes with noble metals can serve by reason of their antiviral or antitumoral properties.

The new phosphonites also have an important indirect utility, as starting materials for the preparation of other phosphorus-containing derivatives, particularly phosphinates, phosphine oxides and phosphinamides. They have the advantage of an excellent diastereoisomeric purity when they have been prepared from an optically-pure difunctional compound (formula 5); their derivatives mentioned above are also of a high optical purity. The importance of this fact is well understood particularly in relation to the synthesis of biologically-active products. Thus, one use of the cyclic phosphonites according to the invention consists of their conversion to phosphinates by the action of an aliphatic or aryl halide; owing to the marked asymmetry of the phosphonite mentioned above, this reaction of opening of the phosphorus-containing ring is considerably improved. In a second stage, by the action of an organo-metallic reactant, a phosphine oxide is obtained; the use of an amide in the second stage gives a phosphinamide.

The non-limitative examples which follow illustrate the invention.

EXAMPLE 1

Preparation of phosphonite —5-dichloroacetamido-4-(4-nitrophenyl)-2-phenyl-1-dioxaphosphorinane (2 R, 4 R, 5 R).

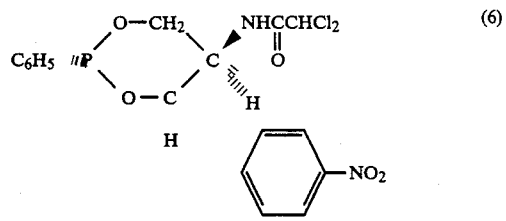

This is the compound of formula (1) in which $R^1$ is a para-nitrophenyl, $R^2$=H, Z is O, Q is CH₂ and Y is <CH—NHCOCHCl₂, that is dichloroacetamido. This is a new compound. The asymmetry of the molecule is characterized here by a ratio of 5 between the molecular weight of the O—CH—C₆H₄NO₂ and the O—CH₂.

Preparation is effected in a 3-neck 1-liter flask, provided with an agitator and two connections serving for the input and removal of the purge nitrogen. 0.03 mole of (+) chloramphenicol (c=2 EtOH) are dissolved at 0° C. in 300 ml of dry THF, with 0.03 mole of dichlorophenylphosphine, under a slow purge with argon. 2.1 equivalents of triethylamine (0.062 mole) are slowly added with agitation. Instantaneously, the reaction occurs and triethylamine hydrochloride precipitates.

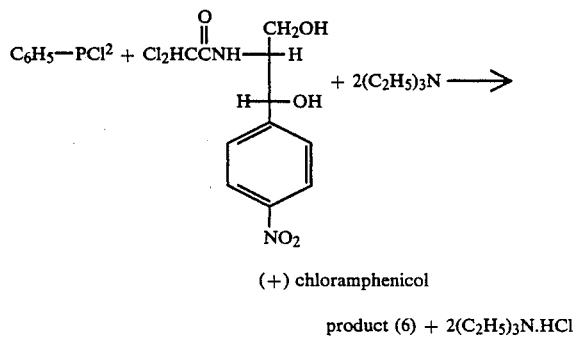

(+) chloramphenicol product (6) + 2(C₂H₅)₃N.HCl

After 1 hour under these conditions, the mixture is filtered, the precipitate is washed with THF and the solvent is evaporated, which allows recovery of 12.5 g of the product in the form of a powder (96% yield) having the following characteristics:

Melts to a paste ~100°.

NMR ¹H (CDCl₃) multiplet (3 H) 3.9 ppm, singulet (1 H) 4.95 ppm, singulet (1 H) 5.2 ppm, multiplet (7 H) 7 ppm, doublet (2 H) 7.7 ppm.

| analysis: | NMR ³¹P (C₆D₆) + 153 ppm | | | |
| --- | --- | --- | --- | --- |
| | C % | H % | N % | O % |
| theory | 47.57 | 3.52 | 6.53 | 18.6 |
| found | 47.55 | 3.95 | 6.24 | 18.96 | rotational power $[\alpha]_D^{20}$ = −100.2° C=20 THF.

IR $\nu_{MH}$=3400 cm⁻¹, $\nu_{C=O}$=1695 cm⁻¹, $\nu_{MO2}$=15-20-1345 cm⁻¹, $\nu_{POC}$=1050 cm⁻¹. Useful in the preparation of catalysts.

EXAMPLE 2

Preparation of (−) 5-dichloroacetamido-4-(4-nitrophenyl)-2-methyl-1,3 2-dioxaphosphorinane (2 R, 4 R, 5 R), that is an analogous phosphonite to that of Example 1, but carrying a CH$_3$— in place of the —C$_6$H$_5$ on the P.

This is also a new compound. It is prepared from dichloromethylphosphine, CH$_3$PCl$_2$ (0.085 mole), (+) chloramphenicol (0.085 mole) and 0.18 mole of triethylamine in ml of THF, according to a mode of operation similar to that of Example 1.

After 1 hour of reaction, the triethylamine hydrochloride is filtered and the solvent evaporated. 29.9 g of dioxaphosphorinane (95% yield) is produced in the form of a powder, which is then recovered.

Melts to a paste: MP: 112° C.

NMR $^1$H (C$_6$D$_6$) doublet (3 H) 1.05 ppm $^2J_{PH}$=12 H$_z$, multiplet (3 H) 3.9 ppm, simplet (1 H) 4.9 ppm, singulet (1 H) 5.25 ppm, doublet (2 H) 7.2 ppm, doublet (2 H) 8.1 ppm.

| NMR $^{31}$P (C$_6$D$_6$) + 170 ppm | | | |
|---|---|---|---|
| analyses: | C % | H % | N % |
| theory | 39.15 | 3.83 | 7.61 |
| found | 38.99 | 3.89 | 7.28 | rotational power $[\alpha]_D^{20}$= −55.2° (C=7.4 THF).
IR $\bar{\nu}_{MH}$=3400 cm$^{-1}$, $\bar{\nu}_{CO}$=1695 cm$^{-1}$, $\bar{\nu}_{MO2}$ 1520−1350 cm$^{-1}$, $\bar{\nu}_{POC}$=1050 cm$^{-1}$.

EXAMPLE 3

Preparation of 5,8-dimethylmethano-5-methyl-2-phenyl-1,3,2-dioxaphosphonane (5 R, 8 S)

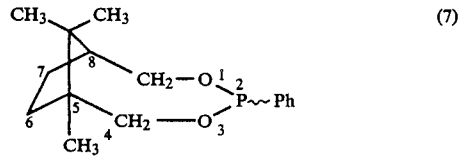

This is a phosphonite of the formula (1) where Q is CH$_2$ and Y is 1,2,2-trimethyl-1,3-cyclopentylene; R$^1$ and R$_2$ are H and Z is oxygen. This is a new compound which has not been described in the technical literature.

The preparation is effected under the same conditions as for Example 1, using 10 g of (+) 1,2,2-trimethyl-bis (hydroxymethyl)-cyclopentane (0.058 mole) and 10.38 g of dichlorophenylphosphine (0.058 mole) in 250 ml of THF.

After filtration of the triethylamine hydrochloride and evaporation of the solvent, the dioxaphosphonane is recovered.

Thick colourless oil

NMR $^1$H C$_6$D$_6$ singulet (3 H) 0.75 ppm, singulet (6 H) 1.05 ppm, multiplet (4 H) 1.35 ppm, multiplet (4 H) 3.85 ppm, multiplet (3 H) 7.15 ppm, multiplet (2 H) 7.8 ppm.

NMR $^{31}$P C$_6$D$_6$ +153 ppm.

EXAMPLE 4

Preparation of the phosphonite oxide: (+) 5-dichloroacetamido-4-(4-nitrophenyl)-2-oxo-1,3,2-dioxaphosphorinahe (2 S, 4 R, 5 R), corresponding to the formula (4), given above, in which the symbols Q, Y, Z and R to R$^2$ are the same as in the formula (6) of Example 1.

This compound is obtained by the oxidation of compound (6) in air. It is new, not having been described in the technical literature.

3 g of dioxaphosphorinane (6) of Example 1 is suspended in 50 ml of toluene and heated in air to 60° for 48 hours. After cooling, 2.5 g of insoluble materials are recovered and taken up in 20 ml of hot CH$_2$Cl$_2$. After filtration of the insoluble materials, crystals of the product (7), which forms in a yield of 20%, are slowly deposited.

Melting point=178°.

NMR $^1$H (DMSO) multiplet (3 H) 4.5 ppm, singulet (1 H) 5.25 ppm, singulet (1 H) 6.5 ppm, multiplet (7 H) 7.5–8 ppm, doublet (2 H) 8.2 ppm.

| NMR $^{31}$P + 28 ppm (CDCl$_3$) analysis: C$_{17}$H$_{15}$O$_6$H$_2$Cl$_2$P | | | | | | |
|---|---|---|---|---|---|---|
| | C % | H % | O % | N % | Cl % | P % |
| calculated | 45.84 | 3.37 | 21.57 | 6.29 | 15.96 | 6.97 |
| found | 45.16 | 3.83 | (21.77) | 6.28 | 15.99 | 6.62 | rotational power :$[\alpha]_D^{20}$+21.7° c=4 (CH$_3$OH).
IR: (KBr) $\bar{\nu}_{CO}$=1670 cm$^{-1}$, $\bar{\nu}_{NH}$=3300 cm$^{-1}$, $\bar{\nu}_{NO2}$=1510–1350 cm$^{-1}$, $\bar{\nu}_{PO}$=1220 cm$^{-1}$.

EXAMPLE 5

Application of the phosphonite of Example 1 to the preparation of (−) methylphenylphosphinate of 2-dichloracetamido-3-iodo-1-(4-nitrophenyl) n.propyl (R$_P$, 1 R, 2 S)

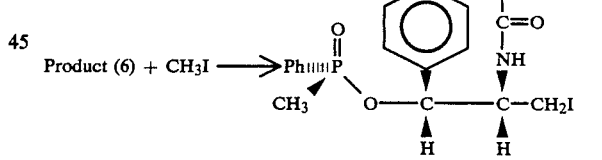

This compound is obtained by the action of methyl iodide on dioxaphosphorinane (6) described in Example 1. This is a new phosphinate which has not been mentioned in the technical literature. Its preparation has been carried out using three different operative modes.

(a) 30 ml of methyl iodide, previously filtered over basic alumina activated for 48 hours at 140° C., are added to 5 g of dioxaphosphorinane (6) in a 250 ml flask. The receptacle is filled with argon, stoppered and held at 60° for 3 hours. The excess halide is evaporated, which gives 6.6 g of the phosphinate in the form of a reddish foam.

(b) In a 250 ml flask, 20 ml of methyl iodide, purified over active alumina, are added to 5 g of dioxaphosphorinane (6) in suspension in 30 ml of benzene. The vessel is filled with argon, stoppered and held for 3 hours at 60° C. Evaporation of the solvent gives 6.5 g of the phosphinate as a reddish foam.

(c) According to a mode of operation identical to (a), the reaction is carried out for 48 hours at the ambient temperature. After evaporation of the halide, 6.5 g of the phosphinate is obtained in the form of a yellow-orange foam.

$^{31}P$, $^1H$ NMR studies and CCM, CPLC chromatography reveal an excellent chemical purity, higher than 95%, and a diastereoisomeric purity of virtually 100% of the phosphinate obtained according to the three procedures a, b, c.

Melts to a paste=95°–100°.

NMR $^1H$ CDCl$_3$ doublet (3 H) 1.9 ppm $^2J_{PH}=14$ H$_Z$, dedoubled doublet (1 H) 3 ppm, dedoubled doublet (1 H) 3.6 ppm, massive (1 H) 4.35 ppm, dedoubled doublet (1 H) 5.6 ppm, singulet (1 H) 6.35 ppm, multiplet (7 H) 7.2–7.8 ppm, doublet (2 H) 8.2 ppm.

NMR $^{31}P$ +46 ppm (CDCl$_3$).

NMR $^{13}C$ (CDCl$_3$).

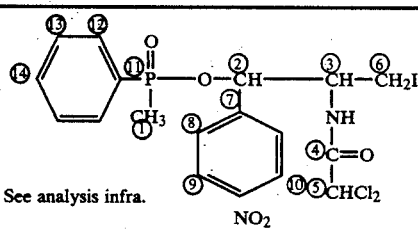

See analysis infra.

| | | | |
|---|---|---|---|
| 1 | 15.45 | ppm | $^1J_{cp} = 102,5$ H$_Z$ |
| 2 | 66.21 | ppm | |
| 3 | 54.49 | ppm | $^3J_{cp} = 3.7$ H$_Z$ |
| 4 | 164.54 | ppm | |
| 5 | 76.44 | ppm | $^2J_{cp} = 6.1$ H$_Z$ |
| 6 | 5.81 | ppm | |
| 7 | 142.88 | ppm | $^3J_{cp} = 3.6$ H$_Z$ |
| 8 | 128.07 | ppm | |
| 9 | 123.71 | ppm | |
| 10 | 148.12 | ppm | |
| 11 | 129.7 | ppm | $^1J_{cp} = 125$ H$_Z$ |
| 12 | 130.9 | ppm | $^2J_{cp} = 9$ H$_Z$ |
| 13 | 128.49 | ppm | $^3J_{cp} = 12.2$ H$_Z$ |
| 14 | 132.86 | ppm | |

Rotational power $[\alpha]_D^{20}=19.6°$ c=9.2 (CH$_3$OH).

IR: (KBr) $\bar{\nu}_{CO}$: 1690 cm$^{-1}$, $\bar{\nu}_{NO2}$: 1520–1345 cm$^{-1}$, $\bar{\nu}_{P=O}$: 1200 cm$^{-1}$, $\bar{\nu}_{POC}$: 1030 cm$^{-1}$.

EXAMPLE 6

Preparation of ethylphenylphosphinate of 2-dichloroacetamido-3-iodo-1-(4-nitrophenyl)-n.propyl (R$_p$, 1 S, 2 S)

This new compound is a homologue of that (8) of Example 5, with CH$_3$CH$_2$— in place of CH$_3$— on the phosphorus:

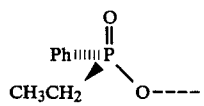

It is obtained by the action of purified ethyl iodide on dioxaphosphorinane (6) of Example 1: the mode of operation is analogous to that of Example 6, with replacement of the methyl iodide by ethyl iodide. The crude product obtained has the form of a yellow powder and contains the desired phosphinate with an excellent chemical purity higher than 95% and a diastereoisomeric purity very close to 100%.

Melts to a paste: ~80°–85°.

The following characteristics are obtained after purification of a sample by chromatography on a Merck Type 5637 silica plate (8 ether - 2 acetone) rf 0.7.

| | NMR $^{31}P$ (CDCl$_3$) + 50 ppm analysis C$_{19}$H$_{20}$O$_5$N$_2$Cl$_2$IP | | |
|---|---|---|---|
| | C % | H % | N % |
| calculated | 38.99 | 3.45 | 4.78 |
| found | 38.66 | 3.68 | 4.73 |

IR: (KBr) $\bar{\nu}_{C=O}$ 1690 cm$^{-1}$, $\bar{\nu}_{P=O}$: 1200 cm$^{-1}$, $\bar{\nu}_{P-O-C}$: 1030 cm$^{-1}$, $\bar{\nu}_{NO2}$: 1520–1345 cm$^{-1}$.

EXAMPLE 7

Preparation of (−) benzylphenylphosphinate of 3-bromo-2-dichloroacetamido-1-(4-nitrophenyl) n.propyl (R$_p$, 1 S, 2 S)

In a similar fashion to Example 6, the new phosphinate homologous to the foregoing has been prepared, carrying a phenyl and a benzyl on the phosphorus:

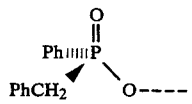

It was obtained by the action of benzyl bromide on the dioxaphosphorinane (6) described in Example 1. The preparation is effected according to a mode of operation similar to that of Example 5(a), by replacing the methyl iodide with benzyl bromide. After reaction for 6 hours, the excess halide is eliminated by distillation under low vacuum. The product has the form of a spongy mass melting to a paste, with an excellent chemical and diastereoisomeric purity. MP≃90°.

NMR $^1H$ (CDCl$_3$) dedoubled doublet (1 H) 2.95 ppm $^2J_{PH}=18$ H$_Z$, doublet (2 H) 3.45 ppm, dedoubled doublet (1 H) 3.6 ppm, massive (1 H) 4.5 ppm, dedoubled doublet (1 H) 5.55 ppm, singulet (1 H) 6.1 ppm, multiplet (12 H) 7.1–7.7 ppm, doublet (2 H) 8.15 ppm.

NMR $^{31}P$ (CDCl$_3$) +42.7 ppm.

rotational power $[\alpha]_D^{20}-6.45°$ c=15 (CHCl$_3$).

EXAMPLE 8

Preparation of (−) benzylmethylphosphinate of 3-bromo-2-dichloroacetamido-1-(4-nitrophenyl) n. propyl (S$_p$, 1 S, 2 S)

This new compound is the homologue of the phosphinate (8) of Example 5 with a benzyl in place of the phenyl on P and a Br in place of I at the end of the chain. Its configuration at the level of the P is:

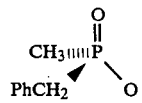

It is obtained by the action of benzyl bromide on the dioxaphosphorinane described in Example 2. The product has the form of a foam melting to a paste. MP=80°–85° C.

NMR $^{31}P$ CDCl$_3$ +52.5 ppm.

IR (KBr) : $\bar{\nu}_{CO}$: 1695 cm$^{-1}$, $\bar{\nu}_{NO2}$: 1520–1350 cm$^{-1}$, $\bar{\nu}_{P=O}$: 1200 cm$^{-1}$, $\bar{\nu}_{POC}$: 1030 cm$^{-1}$.

| Analysis | C % | H % | N % | Cl % | P % |
|---|---|---|---|---|---|
| calculated | 42.4 | 3.74 | 5.20 | 13.17 | 5.76 |
| found | 42.7 | 3.97 | 5.20 | 13.17 | 5.76 | rotational power $[\alpha]_D^{20} = -4.3°$ c=6(CH$_3$OH).

EXAMPLE 9

Use of phosphonite (7) in the preparation of methylphenylphosphinate of [3-iodomethyl-1,2,2-trimethyl-1-cyclopentyl]methyl

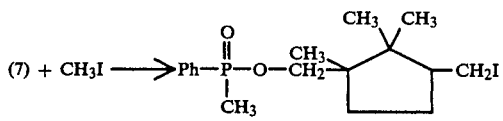

The preparation of the new phosphinate (9) is carried out by the reaction of the dioxaphosphonane (7) of Example 3 with methyl iodide purified over alumina, according to a mode of operation similar to that of Example 5(a). After evaporation of the excess methyl iodide, the phosphinate is obtained in the form of a thick colourless oil.

| NMR $^1$H CDCl$_3$ | doublet | (3 H) | 0.75 ppm |
|---|---|---|---|
| | doublet | (3 H) | 0.95–1.10 ppm |
| | singulet | (3 H) | 1 ppm |
| | massive | | 1.45 ppm |
| | doublet | (3 H) | 1.7 ppm |
| | | | $^2J_{PH} = 14$ H$_Z$ |
| | massive | | 2.25 ppm |
| | multiplet | | 2.8–4.2 ppm |
| | multiplet | (5 H) | 7.45–8.05 ppm |

NMR $^{31}$P = +39 ppm (CDCl$_3$).

IR: $\nu_{P=O}$: 1220 cm$^{-1}$, (See analysis page 21). $\nu_{POC}$: 1020 cm$^{-1}$.

Rotational power $[\alpha]_D^{20} = +42°$ c=5 (CH$_3$OH).

EXAMPLE 10

Preparation of benzylphenylphosphinate of [3-bromomethyl-1,2,2-trimethyl-1-cyclopentyl]methyl This new compound differs from the preceding (9) by a benzyl in place of the methyl on P and by Br in place of I at the end of the chain.

The preparation is carried out according to the following mode of operation: 18 g of dioxaphosphonane (7) and 75 ml of benzyl bromide, purified over alumina, in 100 ml of cyclohexane, are taken to 60° C. for 12 hours, in a sealed 500 ml receptacle under an argon atmosphere. After elimination of the solvent and the excess bromide by distillation under vacuum, 30 g of the new phosphinate is obtained in the form of a thick colourless oil.

| NMR $^1$H (CDCl$_3$) | multiplet | (3 H) | 0.7 ppm |
|---|---|---|---|
| | singulet | (6 H) | 1 ppm |
| | multiplet | (4 H) | 1.4 ppm |
| | multiplet | (1 H) | 2.25 ppm |
| | doublet | (2 H) | 3.35 ppm |
| | | | ($^2J_{PH} = 18$ H$_Z$) |
| | multiplet | (4 H) | 3.6–4 ppm |
| | multiplet | (10 H) | 7.1 to 7.9 ppm |

NMR $^{31}$P (CDCl$_3$) +37.3 ppm.

IR: $\bar{\nu}_{P=O}$: 1200 cm$^{-1}$, $\bar{\nu}_{POC}$: 1000 cm$^{-1}$.

EXAMPLE 11

Use of a Phosphonite in the Preparation of the Oxide of O-anisyl-methylphenylphosphine.

In a first stage, the phosphonite (6) of Example 1 is treated by an alkyl or aryl halide, as in Example 5; then the product obtained (8) is reacted with an organometallic derivative as follows:

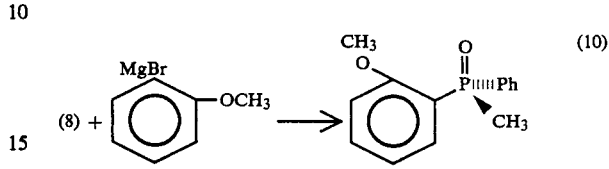

The product (10) is the described precursor of the tertiary diphosphine, diPAMP, used as a catalyst ligand for the industrial preparation of L-Dopa (U.S. Pat. No. 4,008,281 (1975) Monsanto). It is obtained with the R(+) configuration by the reaction of (8) with an excess of orthoanisyl magnesium bromide according to a standard mode of operation (J. Amer. Chem. Soc. 90. 4842, 1968), in toluene under reflux.

By contrast, according to the invention, the same R(+) compound can be obtained by the reaction of (8) for 2 hours with ortho-anisyl lithium in THF at −78°.

| Analysis of Example 5 $C_{18}H_{18}O_5N_2Cl_2IP$ M = 571 | | | | | |
|---|---|---|---|---|---|
| | C | H | N | Cl | P |
| calculated | 37.85 | 3.18 | 4.9 | 12.41 | 5.40 |
| found | 38.05 | 3.23 | 4.68 | 12.08 | 5.11 |

| Analysis of Example 9 $C_{17}H_{26}IO_2P$ M = 420 | | | | | |
|---|---|---|---|---|---|
| | C | H | I | 0 | P |
| calculated | 48.58 | 6.26 | 30.23 | 7.62 | 7.38 |
| found | 48.68 | 6.37 | 30.73 | 7.52 | 7.24 |

EXAMPLE 12

The preparation of (−) 4,4,5-trimethyl 2-phenyl 1,3,2-dioxaphospholane (2R,5 S)

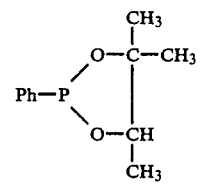

5 g of (+)2 methyl butane 2,3-diol,

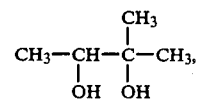

are mixed with 8.6 g of dichlorophenylphosphin at 0° C. under stirring in 250 ml of dry toluene, in an atmosphere. Then 10.2 g of triethylamine are added within a few minutes. After 1 hour of reaction triethylamine hydrochloride is formed; it is separated by filtration and the toluene solvent is vaporized.

An oily residue remains, which is distilled troice in vacuum. Boiling temperature under 1.5 Hg:96° C., colourless liquid.

Yield 60%.

$n_D = 1.525$.

| Analysis: $C_{11}H_{15}O_2P$ molecular weight 210. | | | | |
|---|---|---|---|---|
| % Calculated | C 62.85 | H 7.19 | O 15.22 | P 14.73 |
| % Found | 61.83 | 7.26 | 15.98 | 14.83 |
| RMN $^{31}$P ($C_6D_6$) | = +161.24 ppm | | | |
| (CDCl$_3$) | = +161.33 ppm | | | |
| | RMM$^1$H | | | |
| RMN $^1$H ($C_6D_6$) | 0.95 ppm (d) doublet 3H | | | |
| | 1.05 ppm (d) doublet 6H | | | |
| | 3.55 ppm (q) quadruplet 1H | | | |
| | 7.25 ppm (m) multiplet 3H | | | } 5H |
| | 7.6 ppm (m) multiplet 2H | | | |
| $[\alpha]_D^{20} = -30.8°$ (net) | | | | |

I.R.: (net) 1365–1380 cm$^{-1}$ C(CH$_3$)$_2$; 1070 cm$^{-1}$–905 cm$^{-1}$ (POC).

EXAMPLE 13

When the 2-methyl butane 2,3-diol of example 12 was replaced by 3-propyl hexane 2,3 diol $$CH_3-CH-\underset{\underset{OH}{|}}{\overset{\overset{C_3H_7}{|}}{C}}-CH_2-CH_2-CH_3,$$
$$\phantom{CH_3-}\underset{OH}{|}$$

the oily dioxaphosphalane obtained was 4-methyl 5,5-dipropyl 2-phenyl dioxaphospholane.

EXAMPLE 14

The operations of example 12 were repeated, while dichlorophosphine was replaced by 7.6 g of dichlorobutyl phosphine. Thus 4,4,5 trimethyl 2-butyl 1,3,2 dioxaphospholane is obtained.

EXAMPLE 15

Following the procedure of example 12, 24 g of 1,1-dicyclohexyl propane 1,2-diol (0.1 mol) was mixed with 15.9 g of dichloro-butyl-phosphine (0.1 mol) at +3° C. in 700 ml of dry toluene, under stirring in an argon atmosphere. Then 20.2 g of triethylamine (0.2 mol) are added progressively in 10 minutes.

The mixture is still stirred during one hour; the triethylamine hydrochloride formed is separated by filtration; after the evaporation of toluene, the product obtained is 4-methyl 5,5-dicyclohexyl 2-butyl phospholane:

$$C_4H_9-P\begin{array}{c}O-CH-CH_3\\ \diagup\\ \diagdown\\ O-C-C_6H_{11}\\ |\\ C_6H_{11}\end{array}$$

EXAMPLE 16

2.28 g of (+) -1,1-diphenyl propane 1,2-diol $$CH_3CH-\underset{\underset{OH}{|}}{\overset{\overset{Ph}{|}}{C}}-Ph$$
$$\phantom{CH_3CH-}\underset{OH}{|}$$

are dissolved in 100 ml anhydrous tetrahydrofuranne (THF) at 0° C., together with 1.79 g of dichlorophenyl phosphine. The solution is placed within a 250 ml 2-neck flask provided with a magnetic agitator, and added with 2.12 g of triethylamine.

After one hour stirring at 0° C., the reaction mixture is filtered through a sintered glass (N° 4) filter and the solvent is evaporated. Thus a thick oil is recovered, which crystallizes slowly; the oil is taken off with 20 ml of benzene and the thus formed solution is filtered on millipore. After the evaporation of benzene, 2.7 g of a thick clear-yellow oil are obtained with a yield of 81% which show the following characteristics.

| RMN$^{31}$P | ($C_6D_6$) = +164.56 ppm | | |
|---|---|---|---|
| | (CDCL$_3$) = +164.34 ppm | | |
| RMN$^1$H | (toluene D$_8$) RMM$^1$H | | intensity |
| Ph\\O—Ph\\Ph—P\\O—H\\CH$_3$ | 1 ppm (d) doublet | | 3 H |
| | 4.65 PPM (q)quadruplet | | 1 H |
| | 7.2 to 7.6 ppm(m)multiplet | | 15 H |

$[\alpha]_D^{20} = -245° \pm 25°$ (c = 4.3 toluene)

When heating for several hours a solution in toluene of the above product, in air, then evaporating the toluene and recrystallizing the residue obtained in acetone, the following 2-oxo derivative is obtained: F=190° C.

| RMN $^{31}$P + 29,3 ppm ($C_6D_6$) | | |
|---|---|---|
| RMN $^1$H (CDCl$_3$) | RMN$^1$H | intensity |
| Ph\\O\\O—Ph\\Ph—P\\O—H\\CH$_3$ | 1.35 ppm (d) doublet | 3 H |
| | 5.45 ppm (2g) 2 quadruplet | 1 H |
| | 7.2 to 7.6 ppm(m) multiplet | 15 H |
| Mass spectrum (70 et) | m/e (%) 350 (25) | M$^+$ |
| | m/e (%) 334 (20) | |
| | 306 (100) | |
| | 277 (50) | |
| | 209 (20) | |
| | 192 (90) | |
| | 165 (60) | |
| | 105 (25) | |
| | 77 (25) | |

EXAMPLE 17

Repeating example 1, chloramphenicol is replaced by the same number of molecules of 1-phenyl 3-acetamide propane 1,3-diol $$C_6H_5-\underset{\underset{OH}{|}}{CH}-\underset{\underset{NHCOCH_3}{|}}{CH}-CH_2OH$$

The product obtained is

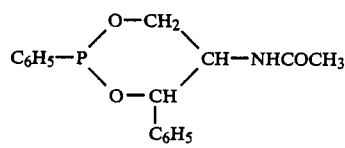

i.e. 5-acetamido 2,4-diphenyl 1,3,2-dioxaphosphorinane.

EXAMPLE 18

The preparation of (+) 4,5-dimethyl 2-phenyl 4,5-1',1',2'-trimethyl 2',5'-cyclopentylene (2'R,5'S) dioxaphospholane-1,3,2 (2S, 4S, 5R).

10 g of (+) dimethyl bornane diol are dissolved in 200 ml of anhydrous THF at 0° C., and the solution is added with 9.04 g of dichlorophenyl phosphine. Then, under stirring in an argon atmosphere, 10.8 g of triethylamine are added. After one hour stirring the amine hydrochloride formed is filtered off. By evaporating the solvent 30.6 g of oil are obtained, which rapidly crystallizes (yield 100%). Melting temperature of the crystals near 50° C.

Analysis: $C_{18}H_{25}O_2P$; M = 304

| | C | H | O | P |
|---|---|---|---|---|
| Calculated %: | 71.03 | 8.28 | 10.51 | 10.17 |
| found %: | 69.56 | 8.37 | 10.08 | 10.02 |

$[\alpha]_D^{21}$ = +7,3° (c = 2, toluene)
 = +3,5° (c = 3.5 THF)
 = +5,6° (c = 8.5 $C_6H_6$)
RMN$^{31}$P ($C_6D_6$) = +157.3 ppm
RMN$^1$H ($C_6D_6$)

| | | | multiplet + intensity 6 singulets |
|---|---|---|---|
| Ha Hb | 0.65 to 2.15 ppm(m + 6 s) | | 20 H |
| Hc | 7.2 ppm (m) | multiplet | 3 H |
| Hd | 7.6 ppm (m) | multiplet | 2 H |

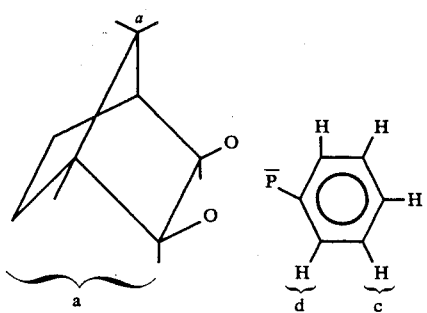

I.R.: 1385-1370 cm$^{-1}$ (C(CH$_3$)$_2$); 1210, 1120 cm$^{-1}$ C—O; 960 cm$^{-1}$ P—O—C.

The dioxaphospholane slowly oxidizes in air and transforms into a 2-oxo compound which melts at 210° C.

EXAMPLE 19

Following the method of example 12, 3-amyl 5-hexene 2,3 diol.

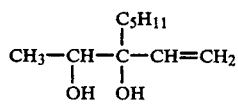

is reacted with dichlorocyclopentyl phophine

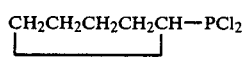

and triethylamine.

4-methyl 5-amyl 5-allyl 2-cyclopentyl 1,3,2-dioxaphane is obtained:

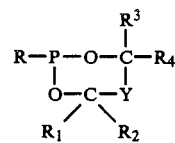

The ratio between the two parts of the molecule $M_2:M_1$ is 3.2.

What is claimed is:

1. Cyclic phosphonite of the formula $$\begin{array}{c} R^3 \\ | \\ R-P-O-C-R_4 \\ | \quad\quad | \\ O-C-Y \\ / \ \backslash \\ R_1 \quad R_2 \end{array}$$

or 5 to 11 ring elements wherein

R is C$_1$ to C$_6$ alkyl, C$_5$ to C$_6$ cycloalkyl or phenyl,

R$^1$ is selected from H, C$_1$ to C$_6$ alkyl, C$_5$ to C$_6$ cycloalkyl or nitrophenyl;

R$^2$ is H, C$_1$ to C$_6$ alkyl, C$_5$ to C$_6$ cycloalkyl, allyl or phenyl;

R$^3$ and R$^4$ are independently H, C$_1$ to C$_6$ alkyl or phenyl;

Y is a bond, —NHC(O)CH$_3$ or —NHC(O)CHCl$_2$ substituted methylene, dimethyl bornanyl or a cyclopentene derivative, the molecule has an asymmetry with respect to a plane perpendicular to the plane of the formula passing through R, P and Y, characterized in that the ratio between the molecular weight M$_1$ of the part of the molecule located on one side of this plane and the molecular weight M$_2$ on the part of the molecule located on the other side of this plane is at least 3 or not greater than ⅓.

2. Compound according to claim 1, M$_1$/M$_2$ ranges from 3 to 10 or from 1/10 to ⅓.

3. Compound according to claim 1, wherein $R^1$ is nitrophenyl.

4. Compound according to claim 1 in which $R^1$, $R^3$ and $R^4$ are H, and $R^2$ is p-nitrophenyl.

5. Compound according to claim 1, constituted by 5-dichloroacetamido-4-(4-nitrophenyl-2-phenyl-1,3,2-dioxaphosphorinane (2R,4R,5R).

6. Compound according to claim 1, constituted by 5,8-dimethylmethano-5-methyl-2-phenyl-1,3,2-dioxaphosphonane (5R,8S).

7. Compound according to claim 1, wherein Y is a bond; R is phenyl, cyclopentyl, cyclohexyl or $C_1$ to $C_6$ alkyl; $R^1$ is H or $C_1$ to $C_6$ alkyl; $R^2$ is $C_1$ to $C_6$ alkyl; $R^3$ is H, phenyl or $C_1$ to $C_6$ alkyl; and $R^4$ phenyl or $C_1$ to $C_6$ alkyl.

8. Compound according to claim 1, wherein $R^1$, $R^2$, $R^3$ and $R^4$ are H and Y is cyclopentylene or cyclohexylene.

9. Compound according to claim 1, constituted by 4-methyl-5,5-diphenyl-1,3,2-dioxaphosphonolane, 4-methyl-5,5-dicyclohexyl-2-butyl-1,3,2-dioxaphosphonolane, 2,4,4-triphenyl-5-methyl-1,3,2-dioxaphosphonolane or 4,5-dimethyl-2-phenyl-4,5-(1′,2′,2′-trimethyl-2′,5′-cyclopentyl (2′R,5′S)-1,3,2-dioxaphosphonolane.

10. Compound according to claim 1, wherein the phosphorous bearing ring has 6 to 9 elements.

11. Compound according to claim 10, constituted by 5-acetamido-2,4-diphenyl-1,3,2-dioxaphosphorinane.

12. Compound according to claim 1 wherein R is methyl, butyl or phenyl; $R^1$ is hydrogen, methyl, cyclohexyl, phenyl or 4-nitrophenyl; $R^2$ is hydrogen, methyl or cyclohexyl, $R^3$ and $R^4$ are hydrogen, methyl or phenyl; and Y is a bond, $NHC(O)CHCl_2$ or $NHC(O)CH_3$ substituted methylene, or a cyclopentene derivative.

13. Compound according to claim 1 in which $R^2$ is hydrogen.

14. Compound according to claim 2 wherein $M_1/M_2$ ranges from 3 to 7 or from 1/7 to ⅓.

* * * * *